United States Patent [19]
Rork et al.

[11] Patent Number: 5,882,682
[45] Date of Patent: *Mar. 16, 1999

[54] CONTROLLED RELEASE SIMVASTATIN DELIVERY DEVICE

[75] Inventors: Gerald S. Rork; James D. Pipkin, both of Lawrence, Kans.

[73] Assignee: Merck & Co., Inc., Rahway, N.J.

[*] Notice: The term of this patent shall not extend beyond the expiration date of Pat. No. 5,366,738.

[21] Appl. No.: 817,129

[22] PCT Filed: Oct. 19, 1995

[86] PCT No.: PCT/US95/13693

§ 371 Date: Aug. 1, 1997

§ 102(e) Date: Aug. 1, 1997

[87] PCT Pub. No.: WO96/12478

PCT Pub. Date: May 2, 1996

Related U.S. Application Data

[63] Continuation of Ser. No. 327,083, Oct. 21, 1994, Pat. No. 5,543,154, which is a continuation-in-part of Ser. No. 118,836, Sep. 8, 1993, Pat. No. 5,366,738, which is a continuation of Ser. No. 902,188, Jul. 29, 1992, abandoned, and a continuation-in-part of Ser. No. 815,304, Dec. 27, 1991, abandoned.

[51] Int. Cl.[6] .................................................... A61K 9/24
[52] U.S. Cl. ........................ 424/473; 424/479; 424/480; 424/489
[58] Field of Search ................................ 424/473, 479, 424/480, 489

[56] References Cited

U.S. PATENT DOCUMENTS

| | | | |
|---|---|---|---|
| 3,146,169 | 8/1964 | Stephenson et al. | 424/466 |
| 4,220,153 | 9/1980 | Dreeback | 128/260 |
| 4,327,725 | 5/1982 | Cortese et al. . | |
| 4,601,893 | 7/1986 | Cardinal | 424/424 |
| 4,743,247 | 5/1988 | Wong | 604/892.1 |
| 4,783,337 | 11/1988 | Wong et al. | 424/468 |
| 4,814,182 | 3/1989 | Graham | 424/468 |
| 4,839,177 | 6/1989 | Colombo et al. | 424/482 |
| 4,898,733 | 2/1990 | DePrince | 424/425 |
| 4,915,954 | 4/1990 | Ayer et al. | 424/473 |
| 4,971,790 | 11/1990 | Magruder | 424/78 |
| 4,994,273 | 2/1991 | Zentner | 424/422 |
| 4,996,060 | 2/1991 | Eckenhoff et al. | 424/473 |
| 5,004,614 | 4/1991 | Staniforth | 424/426 |
| 5,030,452 | 7/1991 | Curatolo | 424/450 |
| 5,051,263 | 9/1991 | Barry | 424/490 |
| 5,057,321 | 10/1991 | Edgren et al. | 424/473 |
| 5,120,548 | 6/1992 | McClelland | 424/473 |
| 5,366,738 | 11/1994 | Rork et al. | 424/473 |

FOREIGN PATENT DOCUMENTS

| | | |
|---|---|---|
| 0 021 758 | 1/1981 | European Pat. Off. . |
| 0 374 404 | 7/1990 | European Pat. Off. . |
| 0 378 404 | 7/1990 | European Pat. Off. . |
| 2 620 025 | 3/1989 | France . |

OTHER PUBLICATIONS

F. Theeuwes, "Elementary Osmotic Pump", Journal of Pharmaceutical Sciences, vol. 64, No. 12, Dec. 1975, pp. 1987–1991.

R. Baker, "Controlled Release of Biologically Active Agents", A Wiley–Interscience Publication, pp. 169–174.

G. M. Zentner, et al., "The Controlled Porosity Osmotic Pump", Journal of Controlled Release, 1 (1985), pp. 269–282.

Primary Examiner—D. Gabrielle Brouillette
Attorney, Agent, or Firm—Carol S. Quagliato; Melvin Winokur

[57] ABSTRACT

Controlled delivery of a beneficial agent in a dispersion is provided using (i) a compressed core which contains the beneficial agent, a polymer which forms gelatinous microscopic particles upon hydration, and if desired, an agent to modulate the hydration; and (ii) a water insoluble coating which adheres to and surrounds the core and contains apertures which provide an area for the hydration and release of the dispersion. The release rate of the beneficial agent is a function of the number and size of the apertures in the coating.

28 Claims, 7 Drawing Sheets

CONTROLLED RELEASE SIMVASTATIN DELIVERY DEVICE

RELATED APPLICATIONS

In accordance with 35 USC 371, this application is a continuation of PCT/US95/13693, which was internationally filed Oct. 19, 1995, and itself is a continuation of U.S. Ser. No. 08/327,083, filed Oct. 21, 1994, now issued as U.S. Pat. No. 5,543,154, which itself is a continuation-in-part of U.S. Ser. No. 08/118,836, filed Sep. 8, 1993, now issued as U.S. Pat. No. 5,366,738, which itself is a continuation of U.S. Ser. No. 07/902,188, filed Jul. 29, 1992, now abandoned, and itself is a continuation-in-part of U.S. Ser. No. 07/815,304, filed Dec. 27, 1991, now abandoned.

FIELD OF THE INVENTION

This invention pertains to both a useful and novel drug-delivery device for dispensing a drug to an environment of use. Particularly, the invention pertains to a system that releases a drug in a controlled fashion, by creating gelatinous microscopic particles of polymer gel and in so doing, generates a dispersion of drug among the microscopic particles. The dispersion then moves from the device surface into the aqueous environment of use.

The device is composed of a core containing a beneficial agent such as a medicament, a polymer which provides gelatinous microscopic particles upon hydration and if desired a hydration modulating agent. The device is completely coated with an insoluble, impermeable coating. The device is completely coated with an insoluble, impermeable coating. The coating contains apertures to expose discrete portions of the surface of the core. The delivery rate of the medicament is a function of the core composition as well as the number and size of the apertures.

In the environment of use, biological fluid contacts the exposed portions of the core surface where hydration of the polymer at the surface begins. As the particles of polymer at the exposed surface absorb water, a gelatinous microscopic dispersion of particles results. Mixed with and dispersed in these microscopic particles are the other components of the core formulation, such as a medicament.

The exposed portion of the core surface is bounded on all sides by the coating. Hydration of the polymer occurs only at the exposed surface of the core, resulting in the steady-state formulation of a gelatinous microscopic particle dispersion within which the drug is dispensed and which moves into the environment of use.

The rate of release of the beneficial agent is not dependent upon the solubility of the beneficial agent in the biological fluid. Rather, the release rate is essentially dependent upon the rate at which the gelatinous microscopic particle dispersion forms at the exposed surface of the device core and exudes from the device carrying with it the beneficial agent and any other core excipient materials that are present.

BACKGROUND OF THE INVENTION

The need for systems that can deliver any drug at a controlled rate of release to an environment of use over a specified period of time is well established.

U.S. Pat. No. 4,814,182 discloses the use of rods or slabs of pre-hydrated and swelled polyethylene oxide hydrogel. The polymer is impregnated with a biologically active agent during the hydration procedure. The hydrated polymer is then dried and partially coated with an impermeable, insoluble material. When placed in an aqueous environment, the polymer swells, but does not dissolve or disintegrate. The entrapped active ingredient is released from the polymer by diffusion. The mechanism of release is based on the ability of the soluble drug to diffuse through the rehydrated hydrogel and move into the aqueous environment.

U.S. Pat. No. 4,839,177 discloses the use of hydrogels compressed to defined geometric forms. In this device, the polymer is mixed with biologically active ingredients to form a core which is affixed to a "support platform" made of an insoluble polymeric material. When hydrated, the swellable, gellable hydrogel expands beyond the device and establishes a superstructure from which the active agent is released either by diffusion, if the active agent is soluble, or by erosion, if the active agent is insoluble. The generation and maintenance of the superstructure is vital to the proper operation of this device.

An osmotic dosage form which utilizes a semipermeable wall containing at least one "exit means" which passes through the wall surrounding a core containing an osmotic agent, a neutral and ionizable hydrogel and an active ingredient is taught in U.S. Pat. No. 4,971,790. The coating of this device is permeable to water from the environment of use. Water moves into the core through the semipermeable membrane. Once inside the device, the water solubilizes the osmotic agent, and hydrates the hydrogels Pressure builds up inside the device, (due to the ionization of the osmogent). Ultimately, the solubilized, ionizable hydrogel, containing the beneficial agent, (the neutral hydrogel) and other core excipients are pumped out of the core, under pressure through an exit means and into the environment of use.

The existing technology is limited since diffusion controlled systems are effective only when soluble active agents are dispensed. For osmotically controlled devices, the technoloy relies upon a wall permeable to the passage of fluid present in the environment of use. Furthermore, these devices require a wall of carefully controlled permeability.

Devices that rely upon the establishment of an extra device superstructure can be altered during in vivo transit, for example, in the gastrointestinal tract. If portions of the superstructure break away, greater surface area is displayed to the environment and unpredictable release of the active agent results.

The usefulness of the above devices would be increased if a device and method were provided to improve the delivery of drugs without regard to their solubility so that diffusion from a swelled polymer or through the superstructure of a polymeric matrix could be avoided. Further utility results from a methodology which provides for a device where the generation of an extra tablet structure could be avoided and the dry ingredients could be contained within a protective coating until release from the device. This would prevent the chance of premature erosion and uncontrolled release of the active agent as well as provide enhanced stability for those active agents that are labile in the fluid of the environment of use.

Figure 1:
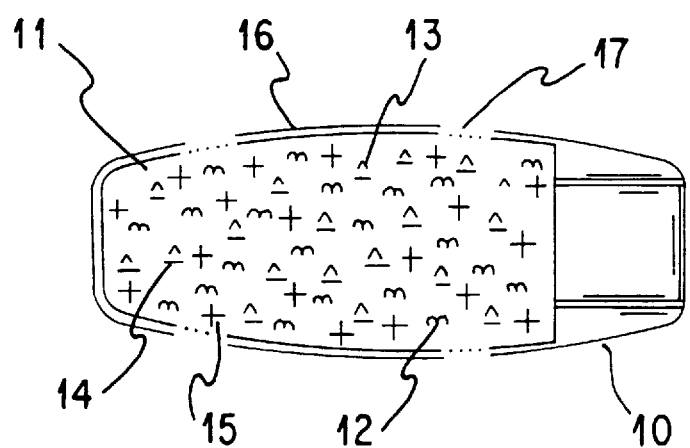
FIG. 1 is a schematic representation of one embodiment of the instant invention. The device 10, has a core composition 11, comprised of a beneficial agent 12, gel forming polymer 13, capable of forming a gelatinous microscopic particle dispersion upon hydration. The core may optionally contain a polymer hydration modulating agent 14 and other tablet forming excipients 15. The core is surrounded by an insoluble, impermeable coating 16, with a plurality of apertures 17 which expose the core surface to the environment of use.

In operation, aqueous solution, from the environment of use, contacts the surface of the core that is exposed within the apertures 17. The available water begins to hydrate the (microscopic gel bead forming) polymer 13 and gelatinous microscopic particles form at the surface of the core. If present, the polymer hydration modulating agent 14, at the exposed core surface, is solubilized and establishes the environment required for controlled hydration of the polymer.

As the polymer particles 13 are hydrated, the gelatinous microscopic particles move from the surface. At the same time, the gelatinous microscopic particles move the beneficial agent 12 from the surrounding surface into the environment as well. These particles of beneficial agent move from the core surface into the environment of use in a dispersion with the gelatinous microscopic particles. As a result, controlling the surface area of the core, which is exposed to the environment of use, effectively controls the delivery rate of medicament to the environment.

The instant invention provides a novel device for delivery of an active or beneficial agent (drug), in a dispersion, and produces a beneficial effect which overcomes the disadvantages associated with prior art devices.

The instant invention also provides a device for delivering an active or beneficial agent, in situ as a suspension, at controlled rate over a specified period of time, which delivery is controlled by the selection of components of the device and not the environment surrounding the device.

Further, the instant invention provides a device for controlled delivery of an beneficial agent where the release rate of the beneficial agent is neither related to the solubility of the beneficial agent nor to the in vivo establishment of an extra tablet superstructure.

Additionally, the instant invention provides a device for controlled delivery of an beneficial agent where delivery occurs from the surface of the device not from within a core so that delivery rate is not dependent on diffusion of the active ingredient from inside the device to the environment Other features and advantages of the invention will be apparent to those skilled in the art from the following detailed description of the invention, taken in conjunction with the drawings and accompanying claims.

DETAILED DESCRIPTION OF THE INVENTION

The novel device of this invention consists essentially of a drug delivery device for the controlled in situ production and release of a dispersion containing a beneficial agent, consisting essentially of:

(A) a compressed core prepared from an admixture comprising
  (i) a therapeutically effective amount of a beneficial agent and
  (ii) a polymer, which upon hydration forms gelatinous microscopic particles;
(B) a water insoluble, water impermeable polymeric coating, which surrounds and adheres to the core, the coating having a plurality of apertures exposing between about 1 and about 75% of the core surface.

By "drug delivery device" is meant, a dosage form that provides a convenient means of delivering a drug to a subject. The subject can be a human or any other animal. The device is designed to be useful for the delivery of a drug by any pharmaceutically accepted means such as by swallowing, retaining it within the mouth until the beneficial agent has been dispensed, placing it within the buccal cavity, or the like.

By "controlled" production is meant that the rate of release of the beneficial agent, that is the amount of beneficial agent released from the device to the environment of use, follows a predetermined pattern. Thus, relatively constant or predictably varying amounts of the beneficial agent can be dispensed over a specified period of time.

The "gelatinous microscopic particles" are composed of discrete particles of hydrated polymer. Both size and hydration rate of these gelatinous microscopic particles are characteristics of the individual polymers. Illustrative of this type of polymer are sodium polyacrylate, particularly those compositions sold under the trade names "AQUAKEEP® J-550", "AQUAKEEP® J-400", which are trade names for sodium acrylate polymer produced by Seitetsu Kagaku Co., Ltd., Hyogo, Japan. The "AQUAKEEP®" polymers are generically described in U.S. Pat. No. 4,340,706. Also illustrative of this type of polymer are carboxypolymethylenes prepared from acrylic acid crosslinked with allyl ethers of sucrose or pentaerythritol and sold under the trade names "CARBOPOL® 934P" and "CARBOPOL® 974P" which are trade names for two carbomer type polymers produced by B. F. Goodrich Chemical Company, Cleveland, Ohio. These latter polymers are generically described in U.S. Pat. No. 2,909,462 and in the National Formulary XVII at p. 1911, CAS Registry Number 9003-01-4. All of the foregoing references are hereby incorporated by reference.

In the dry state, "CARBOPOL 974P" and "CARBOPOL 934P" particles range in size from 2 to about 7 microns. When these articles are hydrated, gelatinous microscopic particles in the range of 20 microns are produced. When "AQUAKEEP J-550" or "AQUAKEEP J-400" particles are hydrated, the diameter of the gelatinous microscopic particles can range in size from 100 to 1000 microns.

Once the drug delivery device is within the environment of use, the polymer of the compressed core which is exposed to the ambient aqueous solution at the coating apertures, begins to hydrate (the polymer) and produce gelatinous microscopic particles. By "in situ production and release of a dispersion" is meant that during the production of the gelatinous microscopic particles, soluble and insoluble core components located near the polymer particles become dispersed and mixed in such a manner that a gelatinous dispersion is produced. The dispersion moves from the device into the aqueous solvent, bringing the beneficial agent into the environment of use. In this novel device, the components of the compressed core move into the environment of use, carried along by the gelatinous microscopic particles, continually exposing new surfaces for further hydration and production of the dispersion.

By ("gel") or "gelatinous" is meant a semisolid system consisting of hydrated polymer interpenetrated by the aqueous solvent of the environment of use.

By "exude" is meant to discharge gradually or emit gradually from the apperatures of the device.

By "compressed core" is meant that an admixture of ingredients comprising a beneficial agent, a polymer which produces gelatinous microscopic particles when hydrated, and other ingredients that may affect any of (1) the rate of production of the dispersion; (2) the stability of the components of the dosage form; or (3) the mixing or compression characteristics of the admixture, is blended in such a way to produce a uniform product. This uniform product is then compressed within a die to produce a desired form, normally in the shape of a tablet, capsule or bolus.

The compressed core contains a therapeutically effective amount of beneficial agent and a polymer which upon hydration results in microscopic gel beads. The term "beneficial agent" broadly includes any drug or mixture thereof that can be delivered from the system to produce a beneficial result. The drug can be soluble in the fluid that makes contact with the exposed surface of the core, or it can be essentially insoluble in the fluid.

In the specification and the accompanying claims, the term "drug" and its equivalents includes any physiologically or pharmacologically active substance that produces a localized or systemic effect or effects in animals. The term "animal" includes mammals, humans and primates such as domestic, household, sport or farm animals such as sheep, goats, cattle, horses and pigs, laboratory animals such as mice, rats and guinea pigs, fishes, avians, reptiles and zoo animals.

The active drug that can be delivered by the novel device of this invention, includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine and hormone systems, immunological system, reproductive system, skeletal systems, autocoid systems, alimentary and excretory systems, inhibitory and histamine systems, and those materials that act on the central nervous system such as hypnotics and sedatives.

Examples of beneficial drugs are disclosed in *Remington's Pharmaceutical Sciences,* 16th Ed., 1980, published by Mack Publishing Co., Eaton, Pa.; *The Pharmacological Basis of Therapeutics,* by Goodman and Gilman, 6th Ed., 1980, published by the MacMillan Company, London; and *The Merck Index,* 11th Edition, 1989, published by Merck & Co., Rahway, N.J. The dissolved drug can be in various forms, such as charged molecules, charged molecular complexes or ionizable salts. Acceptable salts include, but are not limited to hydrochlorides, hydrobromide, sulfate, laurylate, palmitate, phosphate, nitrate, borate, acetate, maleate, malate, succinate, tromethamine, tartrate, oleate, salicylate, salts of metals, and amines or organic cations, for example quaternary ammonium.

Derivatives of drugs such as esters, ethers and amides without regard to their ionization and solubility characteristics can be used alone or mixed with other drugs. Also, a drug can be used in a form that, upon release from the device, is converted by enzymes, hydrolyzed by body pH or other metabolic processes to the original form, or to a biologically active form.

Specific examples of drugs that may be adapted for use include, Angiotensin-converting enzyme (ACE) inhibitors such as enalapril, lisinapril, and captopril; barbiturates such as pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and $\alpha$-bromo-isovaleryl urea; hypnotic and sedative urethanes and disulfanes; psychic energizers such as isocarboxazid, nialamide, imipramine, amitryptyline hydrochloride, pargylene, and protryptyline hydrochloride; tranquilizers such as chloropromazine, promazine, fluphenzaine, reserpine, deserpidine, and meprobamate; benzodiazepines such as diazepam and chlordiazepoxide; anticonvulsants such as primidone, phenytoin, and ethosuximide; muscle relaxants and antiparkinson agents such as mephenesin, methocarbomal, cyclobenzaprine hydrochloride, trihexylphenidyl hydrochloride, levodopa/carbidopa, and biperiden; antihypertensives such as $\alpha$-methyldopa and the pivaloyloxyethyl ester of $\alpha$-methyldopa; calcium channel blockers such as nifedipine, felodipine, diltiazem hydrochloride, diltiazem malate and verapamil hydrochloride; analgesics such as morphine sulfate, codeine sulfate, meperidine, and nalorphine; antipyretics and antiinflammatory agents such as aspirin, indomethacin, ibuprofen, sodium indomethacin trihydrate, salicylamide, naproxen, colchicine, fenoprofen, sulindac, diflunisal, diclofenac, indoprofen and sodium salicylamide; local anesthetics such as procaine, lidocaine, tetracaine and dibucaine; antispasmodics and muscle contractants such as atropine, scopolamine, methscopolamine, oxyphenonium, papaverine; prostaglandins such as $PGE_1$, $PGE_2$, $PGF_{2a}$; antimicrobials and antiparasitic agents such as penicillin, tetracycline, oxytetracycline, chlorotetracycline, chloramphenicol, thiabendazole, ivermectin, and sulfonamides; antimalarials such as 4-aminoquinolines, 8-aminoquinolines and pyrimethamine; hormonal and steroidal agents such as dexamethasone, prednisolone, cortisone, cortisol and triamcinolone; androgenic steroids such as methyltestosterone; estrogenic steroids such as 17$\alpha$-estradiol, $\alpha$-estradiol, estriol, $\alpha$-estradiol 3-benzoate, and 17-ethynyl estradiol-3-methyl ether; progestational steroids such as progesterone; sympathomimetic drugs such as epinephrine, phenylpropanolamine hydrochloride, amphetamine, ephedrine and norepinephrine; hypotensive drugs such as hydralazine; cardiovascular drugs such as procainamide hydrochloride, amyl nitrite, nitroglycerin. dipyridamole, sodium nitrate and mannitol nitrate; diuretics such as chlorothiazide, acetazolamide, methazolamide, hydrochlorothiazide, amiloride hydrochloride and flumethiazide, sodium ethacrynate, and furosemide; antiparasitics such as bephenium, hydroxynaphthoate, dichlorophen and dapsone; antineoplastics such as mechlorethamine, uracil mustard, 5-fluorouracil, 6-thioguanine and procarbazine; $\beta$-blockers such as pindolol, propranolol, metoprolol, oxprenolol, timolol maleate, atenolol; hypoglycemic drugs such as insulin, isophane insulin; protamine zinc insulin suspension, globin zinc insulin, extended insulin zinc suspension, tolbutamide, acetohexamide, tolazamide and chlorpropamide; antiulcer drugs such as cimetidine, ranitidine, famotidine and omeprazole; nutritional agents such as ascorbic acid, niacin, nicotinamide, folic acid, choline, biotin, pantothenic acid; essential amino acids; essential fats; ophthalmic drugs such as timolol maleate, pilocarpine nitrate, pilocarpine hydrochloride, atropine sulfate, scopolamine; electrolytes such as calcium gluconate, calcium lactate, potassium chloride, potassium sulfate, sodium fluoride, ferrous lactate, ferrous gluconate, ferrous sulfate, ferrous fumurate and sodium lactate; and drugs that act on α-adrenergic receptors such as clonidine hydrochloride; analgesic drugs such as acetaminophen, oxycodone, hydrocodone, and propoxyphene; antihypercholesterolemic drugs such as simvastatin, pravastatin, lovastatin and genfibrozil; antiinfective drugs such as cefoxitin, cefazolin, cefotaxime, ciprofloxacin, cephalexin, norfloxacin, amprolium, ampicillin, amoxicillin, cefaclor, erythromycin, nitrofurantoin, minocycline, doxycycline, cefadroxil, miconazole, clotrimazole, phenazopyridine, clorsulon, fludalanine, pentizidone, cilastin, phosphonomycin, imipenem; gastrointestinal drugs such as bethanechol, clidinium, dicyclomine, meclizine, prochlorperizine, trimethobenzamide, loperamide, diphenoxylate, and metoclopramide; anticoagulant drugs such as warfarin, phenindione, and anisindione; 5α-reductase inhibitors such as Proscar and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine, pseudoephedrine, trimethoprim, and ivermectin.

The above list of drugs is not meant to be exhaustive. Many other drugs will certainly work in the instant invention.

By "therapeutically effective amount" is meant that the quantity of beneficial agent contained in the core, which can be delivered to the environment of use, has been demonstrated to be sufficient to induce the desired effect during studies utilizing the beneficial agent.

Other excipients such as lactose, magnesium stearate, microcrystalline cellulose, starch, stearic acid, calcium phosphate, glycerol monostearate, sucrose; polyvinylpyrrolidone, gelatin, methylcellulose, sodium carboxymethylcellulose, sorbitol, mannitol, polyethylene glycol and other ingredients commonly utilized as stabilizing agents or to aid in the production of tablets may also be present in the core.

The drug can be in the core as a dispersion, particle, granule, or powder. Also, the drug can be mixed with a binder, dispersant, emulsifier or wetting agent and dyes.

The active agent may comprise from 0.01% to 75% of the core weight. Generally, the device can house from 0.05 ng to 50 grams of active agent or more, with individual devices containing, for example, 25 ng, about 1 mg, about 5 mg, about 250 mg, about 500 mg, about 1.5 g, or the like.

The "polymer which upon hydration forms gelatinous microscopic particles" useful in the novel device of this invention broadly encompasses any polymer that, upon hydration, is capable of producing discrete gelatinous microscopic particles which support a dispersion, including the beneficial agent, as it forms. The gel forming polymer used also must exude from the core surface in such a way that the beneficial agent is carried into the environment of use. Upon hydration, the gelatinous microscopic particles must be predisposed to leave the surface taking the drug with it. This assures a constant surface area exposed to the solvent of the environment of use and maintains the appropriate rate of release.

Polymers that form usable gelatinous microscopic particles, include the superabsorbant polymers such as "AQUAKEEP J550", "AQUAKEEP J400", "CARBOPOL 974P" and "CARBOPOL 934P" and their pharmaceutically acceptable salts. By "pharmaceutically acceptable salts" of the polymers is meant the acid form of the polymer neutralized by converting all or a portion of the free acid functional groups to their salt form. The core of the device contains from 5% to 75% by weight of the dry microscopic particle polymer.

The "polymer hydration modulator" useful in the novel device of this invention broadly encompasses any water soluble compound that can inhibit or enhance the rate of hydration of the gel forming polymer of the core. Among the groups of compounds that can exert this effect are acids, bases, and the salts of acids and bases such as adipic acid, citric acid, fumaric acid, tartaric acid, succinic acid, sodium carbonate, sodium bicarbonate, betaine hydrochloride, sodium citrate, arginine, meglamine, sodium acetate, sodium phosphates, potassium phosphates, calcium phosphate, ammonium phosphate, magnesium oxide, magnesium hydroxide, sodium tartrate and tromethamine. Other compounds that can be used as polymer hydration modifiers include sugars such as lactose, sucrose, mannitol, sorbitol, pentaerythritol, glucose and dextrose. Polymers such as microcrystalline cellulose and polyethylene glycol as well as surfactants and other organic and inorganic salt can also be used to modulate polymer hydration.

The hydration modulating agents are solubilized by the aqueous media of the environment and establish an environment such that the pH, ionic strength or hydrophilic character is appropriate for the desired polymer microscopic gel bead hydration rate. For example, these hydration modulating agents can enhance or retard the neutralization of acidic functional groups on the polymer which affects the rate of hydration.

The core compartment containing the drug, hydration modulator, and microscopic particle polymer as described herein, is typically in the form of a solid conventional tablet. Generally, the core is compressed into its final shape using a standard tablet compressing machine. The core may contain compressing aids and diluents such as lactose that assist in the production of compressed tablets. The core can be comprised of a mixture of agents combined to give the desired manufacturing and delivery characteristics. The number of agents that may be combined to make the core is substantially without an upper limit with the lower limit equaling two components: the gel forming polymer and the beneficial agent.

The preferred specifications for the core are summarized below and include:

1. Core Drug Loading (size): about 0.01% to about 75% by weight of the total core mass or about 0.05 nanogram to about 50 grams or more (includes dosage forms for humans and animals).

2. Polymer Hydration. Modulator: 0% to about 75% by weight of the total core mass.

3. Gel Forming Polymer: about 5 to about 75% by weight of the total core mass.

In cases where the drug, the gel forming polymer and polymer hydration modulating agent exhibit the desired release rate, stability, and manufacturing characteristics, there is no critical upper or lower limit as to the amount of drug that can be incorporated into a core mass. The ratio of drug to excipient is dictated by the desired time span and profile of release, and the pharmacological activity of the drug.

Generally the core will contain 1% to 50% by weight of an beneficial agent admixed with other solute(s). Representative of compositions of matter that can be released from the device and can function as a solute are, without limitation, those compositions as described.

The coating, applied to the core of the invention, is a material that is impermeable and insoluble in the fluid of the environment of use, can form films, and does not adversely affect the drug, animal body, or host. The coating is impermeable to water and also impermeable to the selected product, drugs, polymer hydration modulating agents, or to other compounds in the device. This impermeable material is insoluble in body fluids and non-erodible or it can be bioerodible after a predetermined period with bioerosion following the end of the active drug release period. In each instance, it is impermeable to solvent and solute(s) and is suitable for construction of the device.

By "impermeable" is meant that the influx of water across the coating is de minimus. Flux of water into the device is via the apertures placed in the coating.

The polymeric coating is applied to and adheres to the entire surface of the core. Apertures are produced in the coating to expose the core, using either a drill, a coring device or any other pharmaceutically accepted means.

The apertures allow liquids from the environment of use to make contact only with exposed portions of the core when in use. The number, size and configuration of the apertures is chosen to provide the release rate required to suit a pharmacologically recognized requirement since the gel dispersion can form only where the apertures allow such core-liquid contact.

The coating can be applied by dipping the cores into a suitable solution of the polymer or by coating the cores with a pharma-acceptable polymer coating process. Among the groups of polymers that can provide this type of protection are cellulose acetate, cellulose acetate butyrate, ethylcellulose, polyvinylacetate, polyvinyl chloride and polymers of acrylic and methacrylic acid esters. In addition, other materials may be included with the coating to enhance its stability, color, elasticity, ease of application or opacity. These include plasticizers such as dibutylsebacate, diethylphthalate, triethylcitrate and polyethylene glycol.

The coating is applied to a thickness of from 1 to 1000 microns but preferably 10 to 500 microns typically, although thinner and thicker coatings fall within the scope of the invention.

The expression "aperture" as used herein, refers to ports through the coating which expose the surface of the core to the environment. The size and number of apertures is chosen to effect the desired release rate. Exposure of from about 1% to about 75% of the core surface is contemplated by this invention.

The apertures are generally positioned in a regular pattern on both faces of the device although they can be positioned anywhere on the core including the edges or all on one face.

The apertures are generally circular but may be of any design that results in the proper release rate. When the aperture is circular, its diameter ranges from about 0.1 mm to about 20 mm with diameters of about 0.2 to 3.5 mm typical. The number of apertures in each device may range from about 2 to about 1000 or more. Typically, the number of apertures in each dosage form ranges from about 5 to about 100.

The apertures may be made by drilling the appropriate size hole through the coating using a mechanical or laser-based process. In the preferred embodiment, a digital laser marking system is used to drill the holes required. This system allows for an array of apertures to be drilled on both faces of a dosage form simultaneously and at rates suitable for production of dosage forms.

The process utilizes a digital laser marking system (for example the DigiMark® variable marking system, available from Directed Energy, Inc.) to produce an unlimited number of holes through the surface or coating of the dosage form, at rates practically suitable for production of dosage forms.

The steps involved in this laser drilling process are as follows: a digital laser marking system is focused at a laser stage; the dosage form is moved onto the laser stage of the digital laser marking system is pulsed to energize those laser tubes needed to drill the desired apertures along a linear array on the dosage form, the dosage form is moved forward on the laser stage and the digital laser marking system is again pulsed as needed to produce an additional linear array of apertures; the dosage form is then removed from the laser stage.

Additional, preferred specifications for the impermeable wall include: a mixture of eight parts by weight of cellulose acetate butyrate, two parts by weight of cellulose acetate and one part by weight of diethylphthalate. This mixture is dissolved in a solution of methylene chloride and methanol (about 3:1 v/v) and sprayed onto the cores to a thickness of about 250 microns. Another preferred coating consists of five parts by weight of cellulose acetate butyrate and one part by weight of triethyl citrate dissolved in a mixture of acetone and methanol (about 3:1 v/v). This mixture is sprayed on the core or dipped into the mixture so that a coating of 100 microns is applied.

The polymers used in the coating which are herein described are known to the art or can be prepared according to the procedures in *Encyclopedia of Polymer Science and Technology,* Vol. 3, published by Interscience Publishers, Inc., New York, in *Handbook of Common Polymers* by Scott, J. R. and Roff, W. J., 1971, published by CRC Press, Cleveland, Ohio.

The following examples illustrate the preparation of the drug delivery device of this invention and their controlled release of one or more therapeutically active ingredients into an environment of use and as such are not to be considered as limiting the invention set forth in the claims appended hereto.

EXAMPLES

In the following examples, the hydroxymethylglutaryl-coenzyme A reductase inhibitors (HMG CoA reductase inhibitors) simvastatin and lovastatin are used as model drugs. These drugs are highly effective in the reduction of serum cholesterol levels in humans and possess neither acidic nor basic functionality. The aqueous solubilities of simvastatin and lovastatin are 0.03 mg/ml and 0.00044 mg/ml respectively, at 20° C. The generation of a dispersion, in situ, from the components of a solid core is disclosed. The anti-arthritic, indomethacin and the analgesic, acetaminophen serve as examples of beneficial agents which are deliverable with this device. This permits the successful formulation of poorly aqueous soluble (simvastatin, lovastatin, indomethacin), moderately soluble (acetominophren) and freely water soluble drugs into a delivery device.

Example 1

Tablets for the controlled release of the drug indomethacin were made as follows, utilizing a 1:1 weight ratio of drug: J-550 polymer.

| Core Component | Weight (g) |
|---|---|
| "AQUAKEEP J-550" | 2 |
| Indomethacin | 2 |
| Avicel PH 101 | 400 mg |
| Povidone (K29-32) | 60 mg in 6 ml EtOH |

Indomethacin, J-550 and Avicel were mixed thoroughly and granulated with the polyvinylpyrrolidone as a 1% by weight solution in ethyl alcohol. The solvated mass was passed through a sieve of standard mesh size 18 then dried overnight at 45° C. Tablet cores were prepared from the resulting granulation by taking approximately 115 mg of the granules and compressing them on a Carver® press using ¼" standard concave punches.

The tablet cores prepared as above were coated with polyvinyl chloride (PVC) coating by dip coating 5 times in diluted clear polyvinyl chloride cement. These tablets were rolled on edge each time on a teflon sheet to prevent sticking. Each tablet was allowed to dry approximately one hour between subsequent coatings and the tablets were dried for approximately 8 hours after the fifth coat was applied. Five 1.5 mm diameter circular openings were drilled through the coating on each face of the tablets.

Figure 2:
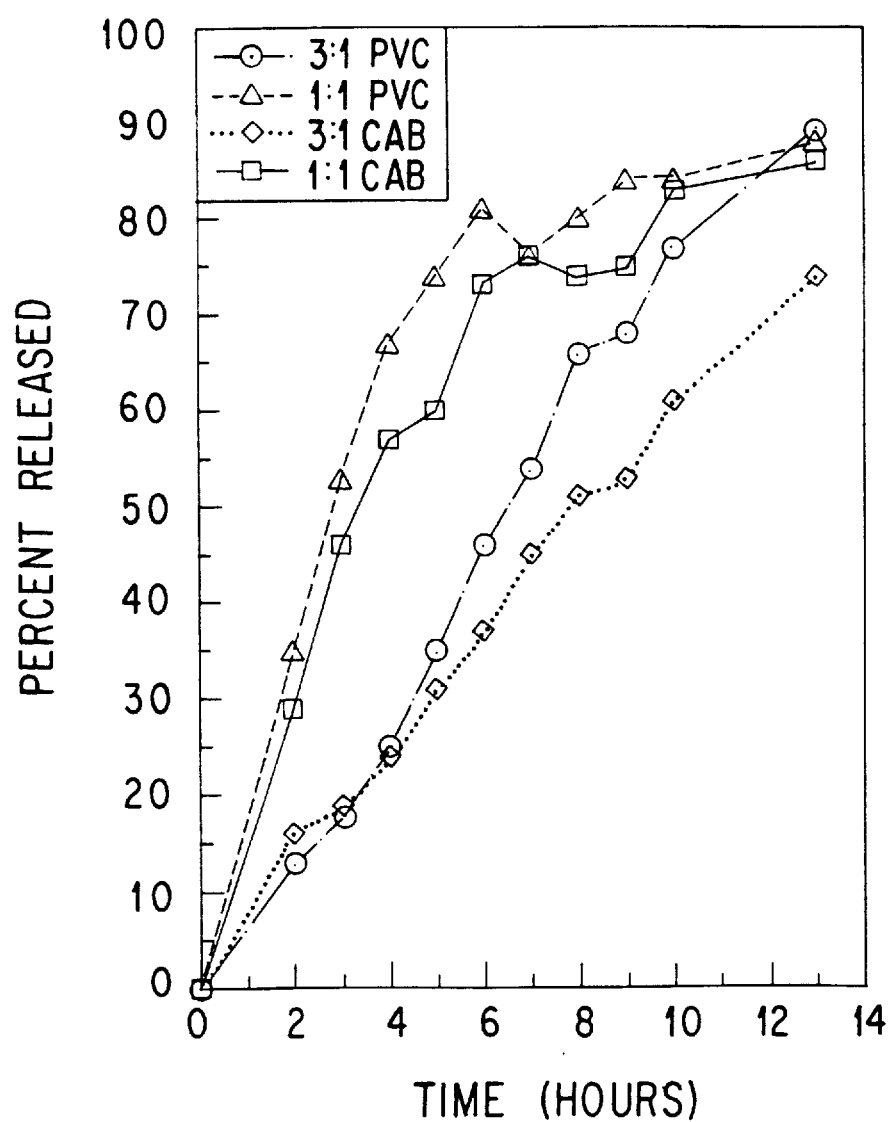
FIG. 2 is a graph showing the percent of drug released over time from devices of the invention, the devices having a drug:core polymer w/w ratio of 1:3: and 1:1 and wherein the coating polymers are polyvinyl chloride (PVC) or cellulose acetate butyrate (CAB). See Examples 1–4.

The release of indomethacin from the coated, drilled tablets into 900 ml of pH 7.5 phosphate buffer at 37° C. with 100 rpm stirring was then determined (USP Apparatus 2). The absorbance of indomethacin was measured at 320 nm using a Cary-14 spectrophotometer. Indomethacin release profiles for the coated, drilled dosage forms are shown in FIG. 2.

Example 2

Tablets were prepared according to the procedure of Example 1, except that the core mixture comprised indomethacin and J-550 polymer in the weight ratio of 1:3. Indomethacin release rates were determined as in Example 1 and are shown in FIG. 2.

Examples 3 and 4

Tablets were prepared according to the procedures of Examples 1 and 2. Core compositions of indomethacin and J-550 in a weight ratio of 1:1 and 1:3 were spray coated with cellulose acetate butyrate CAB 381-20 (Eastman Fine Chemicals) in a Freund® Model HCT-Mini Hi-Coater (8-inch pan) from a methylene chloride:methanol (1:1) solution at 4% by weight solids. Coating thicknesses were 250 microns for the 1:1 indomethacin:J-550 core composition and 400 microns for the 1:3 core composition. The indomethacin release rates were determined as in Example 1 and are shown in FIG. 2.

Example 5

Tablets for the controlled release of simvastatin were prepared from the following formulation:

| Ingredient | mg/Tablet |
|---|---|
| Simvastatin | 100 |
| "AQUAKEEP J-550" | 100 |
| Avicel PH101 | 100 |
| Povidone (K29-32) | 7.8 |
| Magnesium Stearate | 1.5 |
| Total | 309.3 |

The dry ingredients with the exception of magnesium stearate were thoroughly mixed and granulated with absolute alcohol. The solvated mass was passed through a No. 18 stainless steel sieve and then dried for twenty-four hours at 37° C. The dried granules were forced through a No. 35 mesh stainless steel sieve before lubricating with magnesium stearate. This homogeneous mixture was compressed into tablets using ⅜ inch standard concave round punches. The tablets were compressed to a hardness of 19 kg. The tablets were coated in a Freund® Model HCT-Mini Hi-Coater (8-inch pan) to a thickness of 250 microns using the following coating formulation:

| Ingredient | Amount |
|---|---|
| Cellulose Acetate Butyrate CAB 381-20 | 48 g |
| Cellulose Acetate CA 435-75S | 12 g |
| Methylene Chloride | 2250 ml |
| Methanol | 750 ml |
| Diethylphthalate | 6 g |

Figure 3:
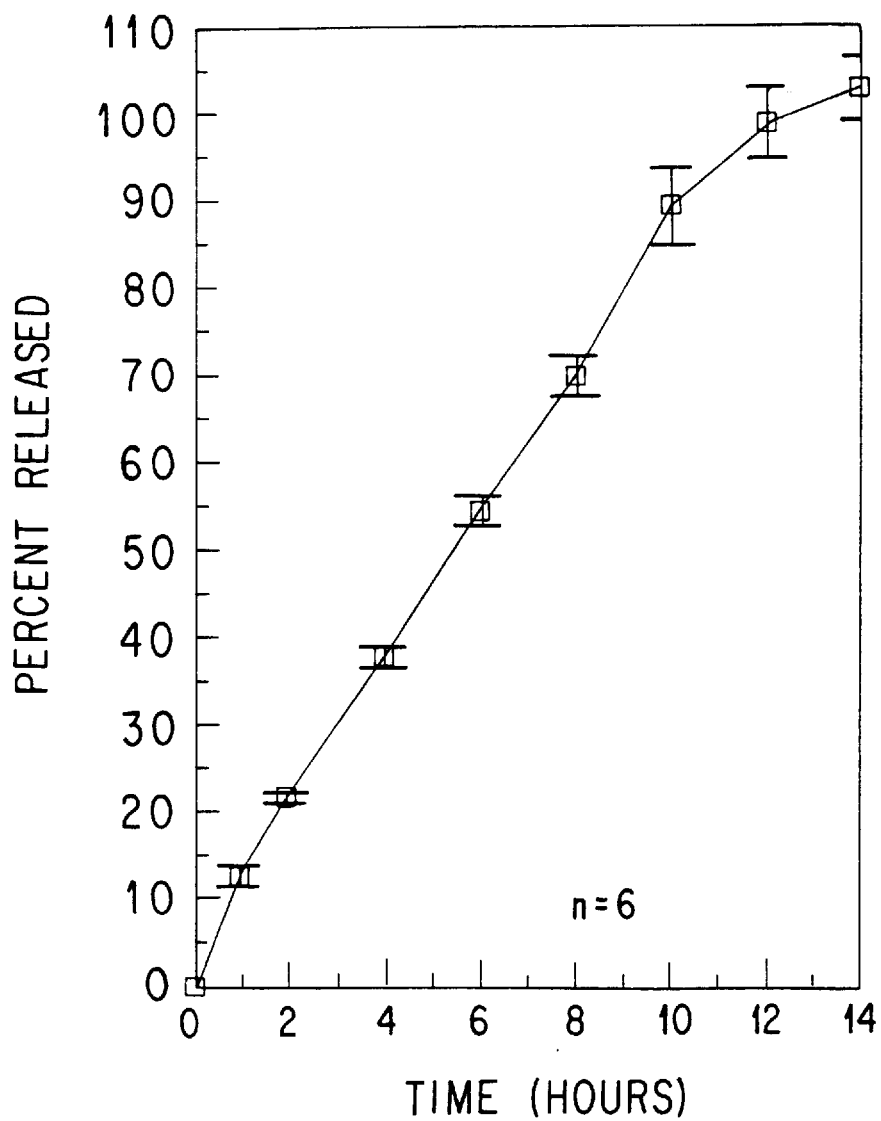
FIG. 3 is a graph showing the percent of drug (simvastatin) released over time from a device of the invention wherein the w/w ratio of drug:core polymer is 1:1 and the polymer coating is cellulose acetate butyrate. See Example 5.

Circular openings in the coating were made using a tubular boring tool with an i.d. of 2.80 mm which provided openings of nearly 3.0 mm. The in vitro release of simvastatin from tablets with three circular openings of 3.0 mm diameter on each face was carried out at 37° C. using USP Apparatus 2 into pH 7.4 phosphate buffer with 0.5% by weight weight sodium dodecyl sulfate at 100 rpm. The results are shown in FIG. 3.

Example 6

Tablets for the controlled release of lovastatin were prepared from the following formulation:

| Ingredient | mg/Tablet |
|---|---|
| Lovastatin | 20 |
| "CARBOPOL 974P" | 13.4 |
| Sodium Citrate Dihydrate | 13.3 |
| Lactose Hydrous (spray dried) | 13.3 |
| Povidone (K29-32) | 3.0 |
| Total | 63.0 |

The ingredients were combined and thoroughly mixed in a mortar and pestle, then granulated with 90% alcohol: 10% by volume water. This wet mass was passed through a No. 20 stainless steel sieve and dried overnight at 40° C. The resulting mixture was compressed into tablets using ¼ inch standard concave punches. The tablets were compressed to a thickness of 2.33 mm and a hardness of 9 kg.

The tablets were coated to a thickness of 250 microns with the following formulation using a Freund® Model HCT-Mini H-Coater (8-inch pan).

| Ingredient | Amount |
| --- | --- |
| Cellulose Acetate Butyrate CAB 381-20 | 64 g |
| Cellulose Acetate CA 435-755 | 16 g |
| Methylene Chloride | 3000 ml |
| Methanol | 1000 ml |
| Diethylphthalate | 8 g |

Figure 4:
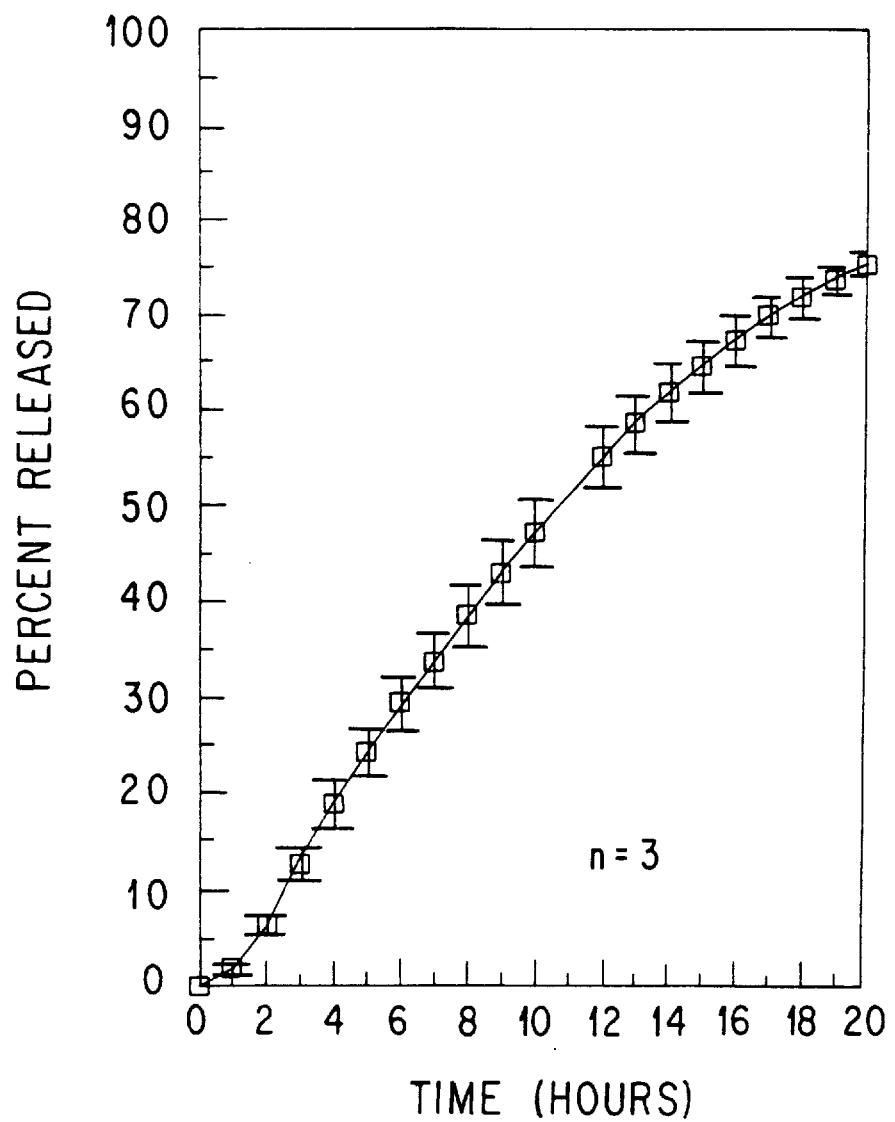
FIG. 4 is a graph showing the percent of drug (lovastatin) released from a device of the invention wherein the w:w ratio of drug:core polymer is 1:1 and the polymer coating is cellulose acetate butyrate. See Example 6

In vitro release tests were carried out at 37° C. using USP Apparatus 2 into pH 7.4 phosphate buffer containing 0.2% sodium dodecyl sulfate at 50 rpm. The drug released was monitored by flow-through UV spectrophotometry. The drug released from coated tablets with 1.75 mm diameter circular openings bored through the coating on each face is shown in FIG. 4.

Example 7

Simvastatin tablets were prepared from the following formulation:

| Ingredients | mg/Tablet |
| --- | --- |
| Simvastatin | 40 |
| CARBOPOL ® 974P | 26.7 |
| Sodium Citrate Dihydrate (milled to 100–200 mesh) | 26.7 |
| Lactose Hydrous NF (spray dried) | 26.6 |
| Povidone USP (K29-32) | 6.0 |
| Butylated Hydroxyanisole NF | 0.04 |
| Magnesium Stearate NF | 0.6 |
| Total | 126.64 |

The simvastatin, CARBOPOL®, milled sodium citrate, lactose and polyvinyl-pyrrolidone were combined, mixed thoroughly and granulated with 10% by weight water in alcohol containing the required BHA. The wet mass was forced through a No. 18 sieve and dried overnight. The dry granulation was lubricated with magnesium stearate and the homogenous mixture compressed using ¼ inch standard concave round tooling and a compression force of 1000 lbs. The compressed tablets had a thickness of 3.89 mm and a hardness of 10 kg. The tablets were spray coated to a coat thickness of 100 microns in a Freund® HCT-Mini Hi-Coater (8-inch pan) using the following coating formulation:

| Ingredient | Amount |
| --- | --- |
| Cellulose Acetate Butyrate CAB 381-20 | 80 g |
| Triethyl Citrate | 16 g |
| Acetone | 3000 ml |
| Methanol | 1000 ml |

Figure 5:
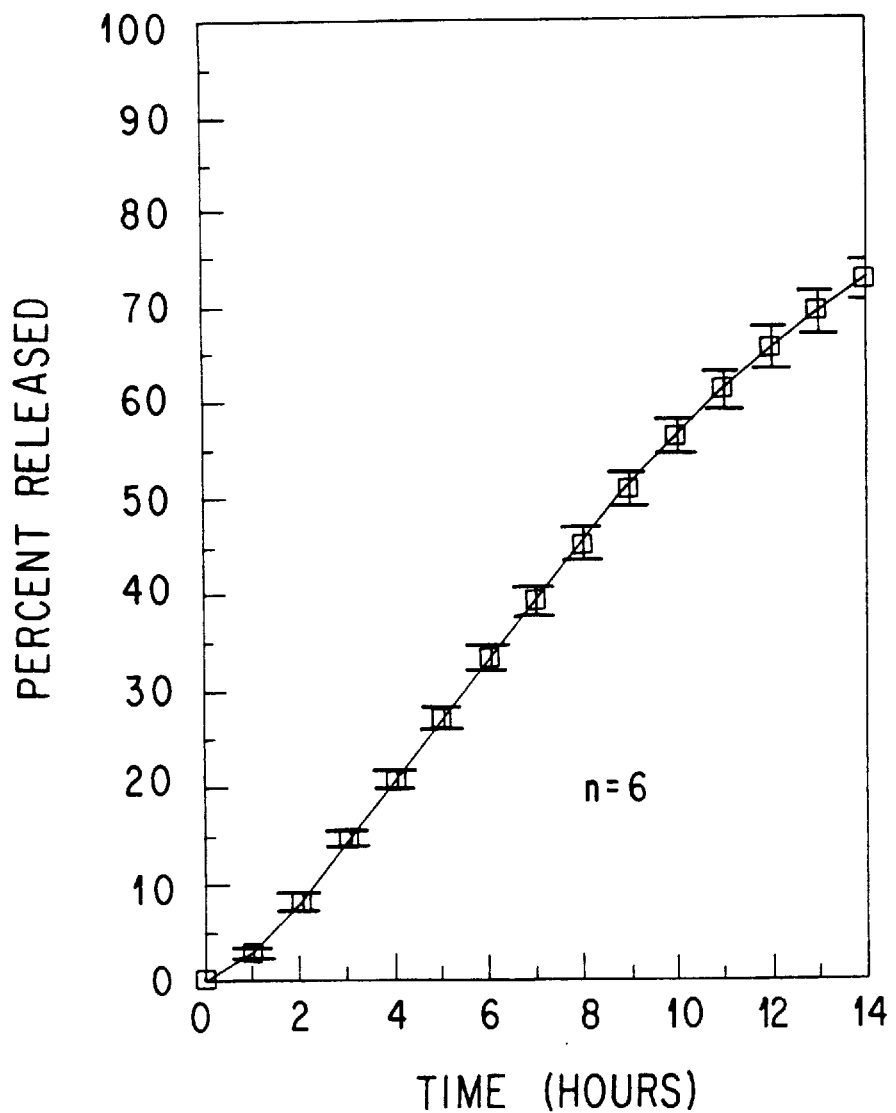
FIG. 5 is a graph showing the percent of drug (simvastatin) released from a device of the invention wherein the w:w ratio of drug:core polymer is 40:26.7 and the polymer coating is cellulose acetate butyrate. See Example 7

In vitro release tests were carried out at 37° C. using USP Apparatus 2 into pH 7.4 phosphate buffer containing 0.4% by weight sodium dodecyl sulfate at 50 rpm. The drug released was monitored by flow-through UV spectrophotometry. The results for tablets with one 2.8 mm diameter circular opening per tablet face are shown in FIG. 5.

Example 8

Tablets for the controlled release of lovastatin were prepared from the following formulation:

| Ingredient | mg/Tablet |
| --- | --- |
| Lovastatin | 40 |
| CARBOPOL 974P NF | 16 |
| Sodium Citrate USP (dihydrate) | 32 |
| Lactose Hydrous NF (spray dried) | 16 |
| Povidone USP (K29-32) | 5.2 |
| Butylated Hydroxyanisole NF | 0.04 |
| Magnesium Stearate NF | 0.55 |
| Total | 109.79 |

The granular sodium citrate dihydrate was reduced in particle size such that 90% by weight went through a No. 120 mesh sieve. The milled sodium citrate dihydrate was combined with lovastatin, CARBOPOL®, lactose and polyvinylpyrrolidone, mixed thoroughly then granulated using Alcohol USP. The solvated mass was passed through a #10 screen then dried overnight at 50° C. The dried granulation was milled, then lubricated with magnesium stearate. The homogeneous mixture was compressed into tablets using ¼ inch standard concave tooling. The tablets were compressed to a thickness of 3.43 mm and a hardness of 10.5 kg. The tablets were coated to a thickness of 100 microns with the following coating formulation using a Glatt WSG-3 fluidized bed column spray coater.

| Ingredients | Amount |
| --- | --- |
| Cellulose Acetate Butyrate (CAB 381-20) | 80 g |
| Triethyl Citrate NF | 16 g |
| Acetone NF | 3000 ml |
| Alcohol USP | 1000 ml |

Figure 6:
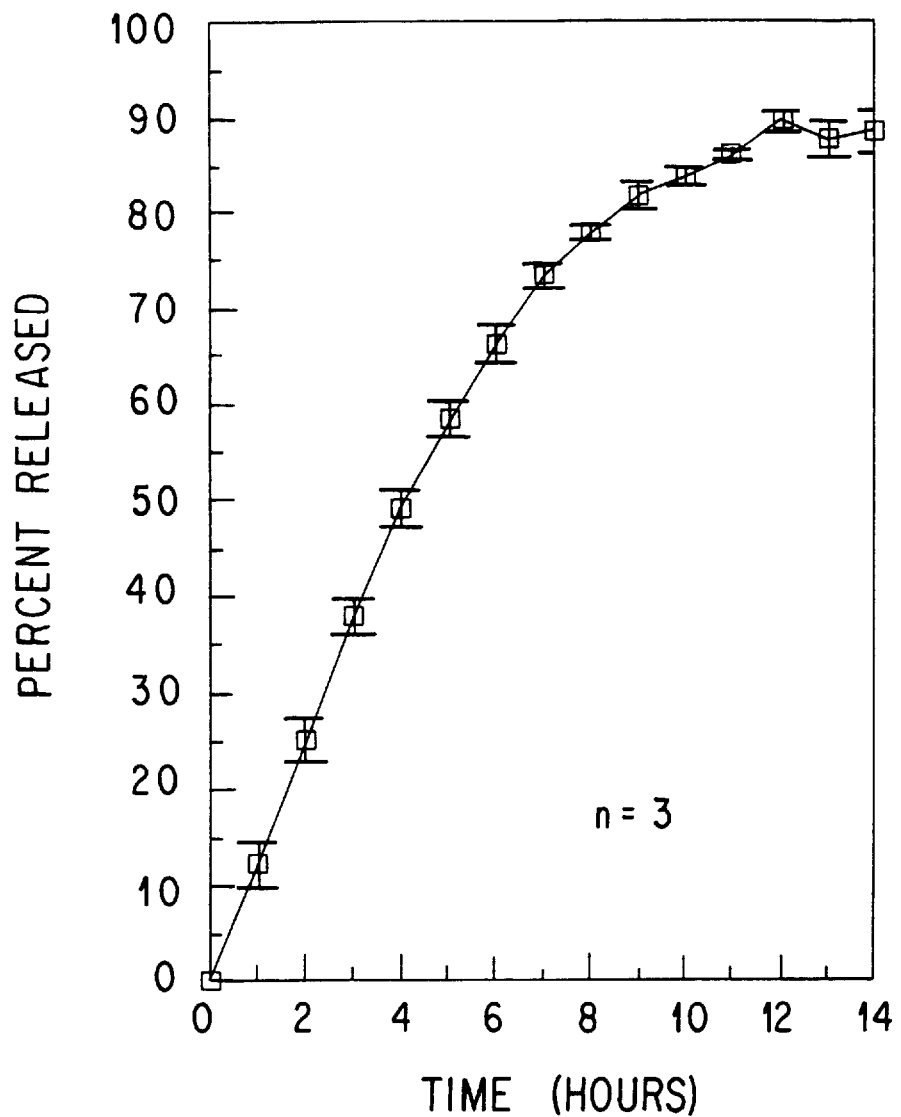
FIG. 6 is a graph showing the percent of drug (lovastatin) released from a device of the invention wherein the w:w ratio of drug:core polymer is 40:16 and the polymer coating is cellulose acetate butyrate. See Example 8

In vitro release tests were carried out as in Example 7 for tablets with bored circular openings of 1.5 mm diameter and three per tablet face. The results are shown in FIG. 6.

Example 9

Tablets for the controlled release of acetaminophen were prepared according to the following formulation:

| Ingredient | mg/Tablet |
| --- | --- |
| Acetaminophen | 20 |
| CARBOPOL ® 974P | 10 |
| Sodium Citrate Dihydrate | 20 |
| Lactose Hydrous (spray dried) | 10 |
| Povidone (K29-32) | 3 |
| Total | 63 |

The ingredients above were combined, mixed thoroughly then granulated with alcohol. The solvated mass was passed through a No. 20 mesh sieve and dried overnight at 40° C. The dried granulation was compressed into tablets using ¼ inch standard concave tooling. The tablets were compressed to a thickness of 2.31 mm and a hardness of 6–7 kg. The tablets were coated as in Example 6.

Figure 7:
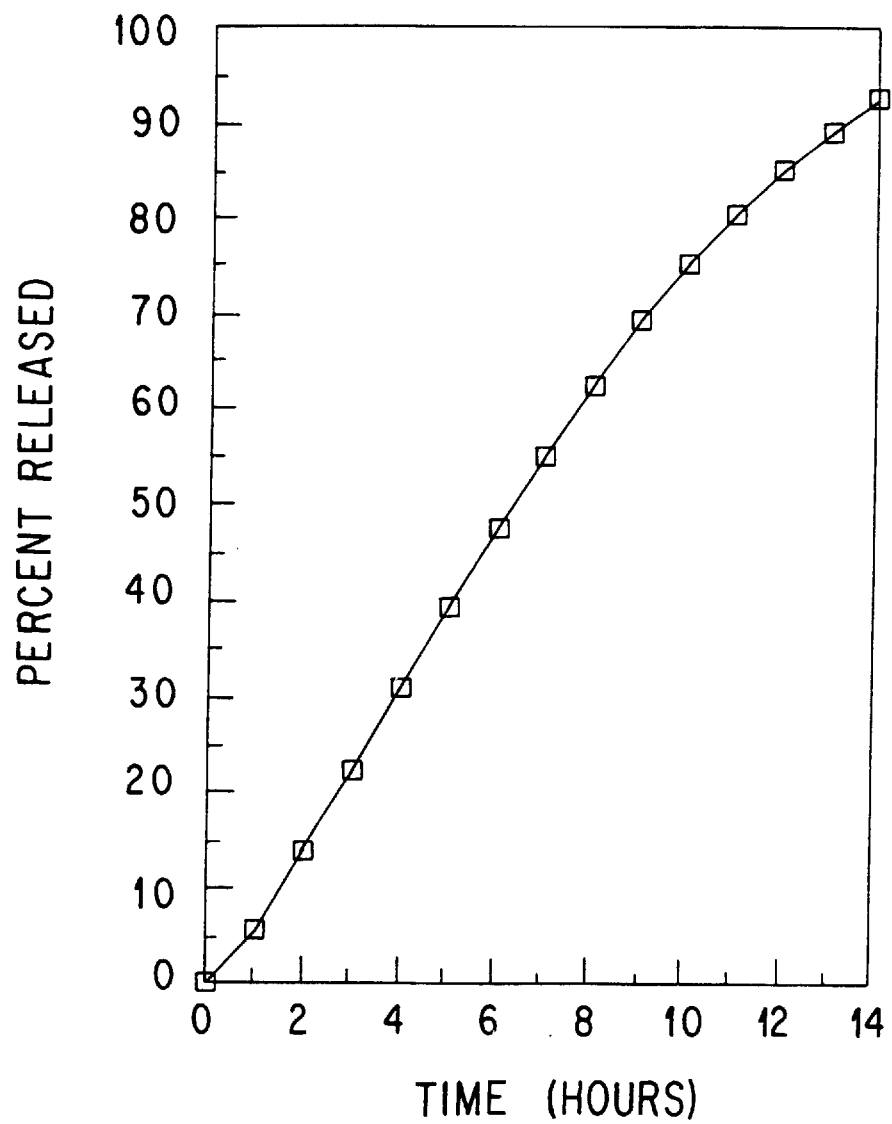
FIG. 7 is a graph showing the percent of drug (acetaminophen) released from a device of the invention wherein the w:w ratio of drug:core polymer is 2:1 and the polymer coating is cellulose acetate butyrate. See Example 9.

In vitro release tests were carried out at 37° C. using USP Apparatus 2 into pH 7.4 phosphate buffer at 50 rpm. The drug released was monitored by flow-through UV spectrophotometry. The results for tablets with one 2.75 mm diameter circular opening per tablet are shown in FIG. 7.

Example 10

Tablets cores containing lovastatin, CARBOPOL® 974P, trisodium citrate and lactose in relations of 5:2:4:2 were prepared using the procedure described in Example 8.

Varying numbers of apertures were mechanically drilled in each face of the coated tablets. The diameter of the apertures ranged from about 0.23 mm to about 3 mm in diameter as measured by microscopic imaging using an Analytical Imaging Concepts IM4000. In vitro release tests wre carried out at 37° C. using USP Apparatus 2 in pH 7.4 phosphate buffer containing 0.4% sodium dodecyl sulfate at 50 rpm. The drug released was monitored by flow-through UV spectrophotometry.

The results of the study are shown in Table I.

Example 11

Twenty-four (24) apertures of 0.35 mm in diameter were drilled in each face of the coated tablets prepared for the study in Example 10 using the DIGIMARK™ digital laser marking system. The apertures were measured by microscopic imaging using an Analytical Imaging Concepts IM4000. Release rates were studied as in Example 10. The results are shown in Table II.

TABLE I

| Number of holes | Initial Drug Release Rate (mg/h) (mg/h) | Hole Diameter (m/m) | Hole Surface Area (m/m$^2$) | Release Rate/Hole Surface Area (mm/h)/mm$^2$ |
|---|---|---|---|---|
| 5  | 0.4  | 0.23 | 0.42  | 1.06 |
| 10 | 0.91 | 0.23 | 0.83  | 1.10 |
| 20 | 2.14 | 0.23 | 1.66  | 1.29 |
| 40 | 3.57 | 0.23 | 3.32  | 1.07 |
| 1  | 0.35 | 0.53 | 0.44  | 0.79 |
| 3  | 1.03 | 0.53 | 1.32  | 0.78 |
| 5  | 1.92 | 0.53 | 2.21  | 0.87 |
| 10 | 3.36 | 0.53 | 4.41  | 0.76 |
| 5  | 4.28 | 1.07 | 8.99  | 0.48 |
| 7  | 5.80 | 1.07 | 12.59 | 0.46 |
| 1  | 1.96 | 1.6  | 4.02  | 0.49 |
| 2  | 3.55 | 1.6  | 8.04  | 0.44 |
| 3  | 5.07 | 1.6  | 12.06 | 0.42 |
| 1  | 2.22 | 2.0  | 6.28  | 0.35 |
| 1  | 2.73 | 2.4  | 9.05  | 0.30 |
| 1  | 4.17 | 3.0  | 14.14 | 0.29 |

TABLE II

| Number of holes | Initial Drug Release Rate (mg/h) | Hole Surface Area (m/m$^2$) | Release Rate/Hole Surface Area (mg/h)/mm$^2$ |
|---|---|---|---|
| 24 | 3.96 | 4.62 | 0.86 |

Example 12

Tablets for the controlled release of nifedipine were prepared from the following formulation:

| Ingredient | mg/Tablet |
|---|---|
| Nifedipine micronized | 69 |
| CARBOPOL 974P NF | 30 |
| Dibasic Sodium Phosphate (anhydrous) USP | 75 |
| Lactose Hydrous NF (spray dried) | 15 |
| Povidone USP K-90 | 5 |
| Magnesium Stearate NF | 0.88 |
| Total | 194.88 |

The nifedipine was milled using the Model 00 Jet-O-Mizer to a 10 micron median particle size. The micronized nifedipine was combined with dibasic sodium phosphate, carbopol, lactose and polyvinylpyrrolidone, mixed thoroughly then granulated using an aqueous alcoholic solvent blend (10% by volume water). The solvated mass was passed through a #20 screen then dried initially at 60° C. for two to four hours, then at 40° C. overnight. Magnesium stearate was sifted over the dried granulation and the total mixture passed through a #40 screen. The homogenous mixture was compressed into tablets using ⁵⁄₁₆ inch standard concave tooling. The tablets were compressed to a thickness of 3.6 mm and a hardness of 20 kg. The tablets were coated to a thickness of 100 microns with the following coating formulation using a UniGlatt fluidized bed column spray coater.

| Ingredient | Amount |
|---|---|
| Cellulose Acetate Butyrate (Eastman 381-20) | 140 g |
| Triethyl Citrate NF | 14 g |
| Methylene Chloride | 3000 ml |
| Alcohol USP | 1000 ml |

The tablets were mechanically drilled with 18–0.45 mm diameter opening through the coating on each face then overcoated to a thickness of approximately 150 microns with the following coating formulation using a UniGlatt fluidized bed column spray coater.

| Ingredient | Amount |
|---|---|
| Hydroxypropyl Methylcellulose (Methocel E5) | 100 g |
| Ethylcellulose (Ethocel E10) | 25 g |
| Water | 100 ml |
| Alcohol | 1000 ml |
| Methylene Chloride | 2500 ml |

In vitro release tests were carried out at 37° C. using USP Apparatus 2 into pH 7.4 phosphate buffer containing 2% sodium dodecyl sulfate at 100 rpm. The drug released was monitored by flow-through UV spectrophotometry at 340 nm.

What is claimed is:

1. A drug delivery device for the controlled in situ production and release of a dispersion containing simvastatin, which is:
   (A) a compressed core prepared from an admixture comprising:
      (i) a therapeutically effective amount of simvastatin; and
      (ii) a polymer which upon hydration forms gelatinous microscopic particles, wherein the polymer is selected from the group consisting of sodium polyacrylate, carboxypolymethylenes, and the pharmaceutically acceptable salts thereof, and wherein the carboxypolymethylenes are prepared from acrylic acid crosslinked with allylethers of sucrose or pentaerythritol; and
   (B) a water insoluble, water impermeable polymeric coating comprising a polymer and a plasticizer, which surrounds and adheres to the core, wherein the polymer is selected from the group consisting of cellulose acetate, cellulose acetate butyrate, ethylcellulose, polyvinylacetate, polyvinyl chloride, polymers of acrylic and methacrylic acid esters, and combinations of these polymers, and the plasticizer is selected from the group consisting of dibutylsebacate, diethylphthalate, triethylcitrate and polyethylene glycol, the coating having a plurality of formed apertures exposing between about 1 and about 75% of the core surface;

and wherein the release rate of the beneficial agent from the device is a function of the number and size of the apertures.

2. The device of claim 1 wherein the amount of simvastatin in the core comprises from 0.01% to 75% by weight of the core mixture.

3. The device of claim 1 wherein the amount of polymer which upon hydration produces gelatinous microscopic particles in dry form comprises from about 5% to about 75% by weight of the core mixture.

4. The device of claim 1 wherein the water insoluble, water impermeable polymeric coating is comprised of a polymer selected from the group consisting of polyvinyl chloride, cellulose acetate, cellulose acetate butyrate, ethylcellulose and combinations of these polymers; and a plasticizer selected from the group consisting of diethylphthalate, dibutylsebacate and triethylcitrate.

5. The device of claim 1 wherein the polymer in the water insoluble, water impermeable polymeric coating is cellulose acetate butyrate.

6. The device of claim 1 wherein the plasticizer in the water insoluble, water impermeable polymeric coating is triethylcitrate.

7. The device of claim 1 wherein the polymer which upon hydration forms gelatinous microscopic particles is selected from the group consisting of carboxypolymethylenes prepared from acrylic acid crosslinked with allylethers of sucrose or pentaerythritol, and the pharmaceutically acceptable salts thereof.

8. The device of claim 1 wherein the compressed core further comprises at least one polymer hydration modulating agent selected from the group consisting of acids, bases, salts, sugars, surfactants, and soluble polymers.

9. The device of claim 8 wherein the polymer hydration modulating agent or agents are selected from the group consisting of sodium phosphates and microcrystalline cellulose.

10. The device of claim 1 wherein the compressed core is further comprised of one or more compressing aids and diluents.

11. The device of claim 1 wherein the compressed core is further comprised of lactose.

12. The device of claim 1 wherein the apertures in the coating range from 0.1 mm to 20 mm at their widest point.

13. The device of claim 1 wherein the number of apertures ranges from 2 to 1000.

14. The device of claim 13 wherein the number of apertures ranges from 5 to 100.

15. The device of claim 1 wherein the apertures are positioned in a regular pattern on both faces of the device.

16. The device of claim 1 further comprised of at least one material for enhancing at least one of the characteristics of the water impermeable polymeric coating, wherein the characteristics are selected from the group consisting of stability, color, elasticity, ease of application, and opacity.

17. The device of claim 16 comprised of at least one material for enhancing the elasticity of the water impermeable polymeric coating.

18. The device of claim 16 comprised of at least one material for enhancing the opacity of the water impermeable polymeric coating.

19. The device of claim 16 comprised of at least one material for enhancing the ease of application of the water impermeable polymeric coating.

20. A drug delivery device for the controlled in situ production and release of a dispersion containing simvastatin, which is:

(A) a compressed core prepared from an admixture comprising:
  (i) from 0.01% to 75% by weight of the core mixture of a therapeutically effective amount of simvastatin; and
  (ii) from about 5% to about 75% by weight of the core mixture of a polymer which upon hydration forms gelatinous microscopic particles, wherein the polymer is selected from the group consisting of sodium polyacrylate, carboxypolymethylenes and the pharmaceutically acceptable salts thereof, and wherein the carboxypolymethylenes are prepared from acrylic acid crosslinked with allylethers of sucrose or pentaerythritol; and (B) a water insoluble, water impermeable polymeric coating comprising a polymer and a plasticizer, which surrounds and adheres to the core, wherein the polymer is selected from the group consisting of polyvinyl chloride, cellulose acetate, cellulose acetate butyrate, ethylcellulose and combinations of these polymers, and the plasticizer is selected from the group consisting of diethylphthalate, dibutylsebacate and triethylcitrate, the coating having a plurality of formed apertures exposing between about 1 and about 75% of the core surface;

and wherein the release rate of drug from the device is a function of the number and size of the apertures.

21. The device of claim 20 wherein:
  the polymer which upon hydration forms gelatinous microscopic particles is selected from the group consisting of carboxypolymethylenes prepared from acrylic acid crosslinked with allylethers of sucrose or pentaerythritol and the pharmaceutically acceptable salts thereof;
  the polymer in the water insoluble, water impermeable polymeric coating is cellulose acetate butyrate; and
  the plasticizer in the water insoluble, water impermeable polymeric coating is triethylcitrate.

22. The device of claim 21 wherein the compressed core is further comprised of at least one polymer hydration modulating agent selected from the group consisting of sodium phosphates and microcrystalline cellulose.

23. A process for the preparation of a drug delivery device for the controlled in situ production and release of a dispersion containing a beneficial agent characterized by having a compressed core surrounded by a water insoluble, water impermeable polymeric coating, comprising the steps of:

(A) preparing a uniform mixture by either dry mixing or wet granulating a polymer which upon hydration produces gelatinous microscopic particles, the beneficial agent and other excipients used in the preparation of the core, wherein the polymer is selected from the group consisting of sodium polyacrylate, carboxypolymethylenes, and the pharmaceutically acceptable salts thereof, and wherein the carboxypolymethylenes are prepared from acrylic acid crosslinked with allylethers of sucrose or pentaerythritol;

(B) compressing the uniform mixture into cores;

(C) coating the entire core with the water insoluble, water impermeable polymeric coating comprised of a polymer and a plasticizer, wherein the polymer is selected from the group consisting of cellulose acetate, cellulose acetate butyrate, ethylcellulose, polyvinylacetate, polyvinyl chloride, polymers of acrylic and methacrylic acid esters, and combinations of these polymers, and the plasticizer is selected from the group consisting of dibutylsebacate, diethylphthalate, triethylcitrate and polyethylene glycol; and (D) forming apertures through the coating.

24. The process of claim 23 wherein the beneficial agent is simvastatin.

25. The process of claim 23 wherein the uniform mixture of step (A) is prepared by either dry mixing or wet granulating a polymer hydration modulating agent with the polymer, the beneficial agent and the other excipients.

26. The process of claim 25 wherein at least one material for enhancing at least one of the characteristics of the water impermeable coating is added either before or after, or before and after, application of the water impermeable polymeric coating, wherein the characteristics are selected from the group consisting of stability, color, elasticity, ease of application, and opacity.

27. The process of claim 26 wherein the beneficial agent is simvastatin.

28. A drug delivery device for the controlled in situ production and release of a dispersion containing simvastatin, which is:

(A) a compressed core prepared from an admixture comprising:

(i) a therapeutically effective amount of simvastatin; and (ii) a polymer which upon hydration forms gelatinous microscopic particles, wherein the polymer is selected from the group consisting of sodium polyacrylate, carboxypolymethylenes, and the pharmaceutically acceptable salts thereof, and wherein the carboxypolymethylenes are prepared from acrylic acid crosslinked with allylethers of sucrose or pentaerythritol; and (B) a water insoluble polymeric coating comprising a polymer and a plasticizer, which surrounds and adheres to the core, wherein the polymer is selected from the group consisting of polyvinyl chloride, cellulose acetate, cellulose acetate butyrate, ethylcellulose and combinations of these polymers, and the plasticizer is selected from the group consisting of diethylphthalate, dibutylsebacate, and triethylcitrate, the coating having a plurality of formed apertures exposing between about 1 and about 75% of the core surface; and wherein the release rate of the beneficial agent from the device is a function of the number and size of the apertures.

\* \* \* \* \*